(12) United States Patent
Godavarty et al.

(10) Patent No.: US 11,471,696 B1
(45) Date of Patent: Oct. 18, 2022

(54) HANDHELD DEVICES FOR WOUND ASSESSMENT USING MULTI-MODAL IMAGING

(71) Applicants: Anuradha Godavarty, Miami, FL (US); Kacie Kaile, Miami, FL (US)

(72) Inventors: Anuradha Godavarty, Miami, FL (US); Kacie Kaile, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/590,436

(22) Filed: Feb. 1, 2022

(51) Int. Cl.
| | | |
|---|---|---|
| *A61N 5/06* | (2006.01) | |
| *A61B 5/01* | (2006.01) | |
| *A61B 5/00* | (2006.01) | |
| *A61B 5/1455* | (2006.01) | |
| *A61N 5/067* | (2006.01) | |
| *H04N 5/225* | (2006.01) | |
| *G06T 11/00* | (2006.01) | |
| *H04N 13/239* | (2018.01) | |
| *H04N 5/247* | (2006.01) | |

(52) U.S. Cl.
CPC ............ *A61N 5/0616* (2013.01); *A61B 5/015* (2013.01); *A61B 5/14556* (2013.01); *A61B 5/742* (2013.01); *A61N 5/067* (2021.08); *G06T 11/00* (2013.01); *H04N 5/2256* (2013.01); *H04N 5/247* (2013.01); *H04N 13/239* (2018.05); *A61B 2560/0431* (2013.01); *A61N 2005/0626* (2013.01); *A61N 2005/0651* (2013.01)

(58) Field of Classification Search
CPC ...... A61N 5/0616; A61N 5/067; A61N 5/015; A61N 5/14556; A61N 5/742; A61N 2005/0626; A61N 2005/0651; H04N 13/239; H04N 5/2256; H04N 5/247; G06T 11/00; A61B 2560/0431

See application file for complete search history.

(56) References Cited

U.S. PATENT DOCUMENTS

| | | | | |
|---|---|---|---|---|
| 9,042,967 | B2 * | 5/2015 | Dacosta | A61B 5/742 600/476 |
| 2015/0238774 | A1 * | 8/2015 | Anderson | A61K 35/04 604/20 |
| 2017/0270350 | A1 * | 9/2017 | Maltz | G16H 30/40 |
| 2019/0008387 | A1 * | 1/2019 | Godavarty | G06T 7/62 |
| 2019/0216326 | A1 * | 7/2019 | Cross | G03B 29/00 |
| 2020/0364862 | A1 * | 11/2020 | DaCosta | G06T 7/0012 |
| 2022/0061671 | A1 * | 3/2022 | DaCosta | A61B 5/4842 |

* cited by examiner

*Primary Examiner* — Catherine M Voorhees
*Assistant Examiner* — Roland Dinga
(74) *Attorney, Agent, or Firm* — Saliwanchik, Lloyd & Eisenschenk

(57) ABSTRACT

Multi-modal, portable, handheld devices for tissue assessment (e.g., wound assessment) are provided, as are methods of fabricating and methods of using the same. The devices can be used for virtual medicine (VM)-based wound management, such as VM-based diabetic foot triage (DFT) and management. The device can be used to take physiological measurements of temperature and/or tissue oxygenation of a wound to assess the wound, for example in a remote setting environment. The device can also be used to provide therapy for tissue repair and/or wound healing, apart from the multi-modal imaging of the tissue surface of the patient. For example, light therapy, such as low-level light therapy (LLLT) can be provided via one or more light emitting diodes (LEDs) and/or laser diodes.

17 Claims, 6 Drawing Sheets

HANDHELD DEVICES FOR WOUND ASSESSMENT USING MULTI-MODAL IMAGING

BACKGROUND

Complications from Diabetes Mellitus (DM) are increasing, making DM a major global health problem. One in three patients with DM develops diabetic foot ulcers (DFUs) during their lifetime, and this is a major risk factor for amputation and mortality. Wound care management is rapidly expanding in treatment and preventive measures of DFUs. One of the major challenges of DFU treatment is patient compliance and the irregular clinical visits of patients, which decelerates healing. Non-compliance with regular care and follow-up of chronic DFUs can lead to hospitalization or amputations from severe infections.

BRIEF SUMMARY

In view of the above-mentioned challenges, clinicians must adopt a paradigm shift from hospital and clinic care to community-based care or patient self-care. Virtual Medicine (VM) can greatly impact diabetic foot ulcer (DFU) wound care management with tools for remote monitoring of patients. Remote patient monitoring (RPM) shows great promise in identifying areas of impending injury/tissue loss for not only DFUs but also for those who have not yet ulcerated, as well as the presence or absence of infection. No related art low-cost mobile-based VM technology exists that can provide comprehensive (and multiple) clinical assessments towards diabetic wound care management and/or prevention during RPM.

Embodiments of the subject invention provide novel and advantageous multi-modal, portable, handheld (e.g., smartphone, tablet, or separate standalone device) imaging technology that can be used for wound assessment (e.g., remote wound assessment, such as remote diabetic wound assessment), both visual and physiological, for VM-based wound management (e.g., VM-based diabetic foot triage (DFT) and management). Embodiments also provide methods of fabricating the devices and using the devices, as well as data acquisition and analysis procedures. The device can be used to take physiological measurements of temperature and/or tissue oxygenation (TO), and/or digital photographs (e.g., digital color photographs), of a target area (e.g., a wound or wound site) of a patient (e.g., a human patient) to provide assessment (e.g., sub-clinical assessment) to replace, or complement the visual gold-standard clinical assessment (i.e., wound size, color, and epithelization), especially in a remote setting environment. The device can also be used to provide therapy for tissue repair and/or wound healing, apart from the multi-modal imaging of the tissue surface of the patient. For example, light therapy, such as low-level light therapy (LLLT) can be provided (e.g., via one or more light emitting diodes (LEDs), such as one or more LEDs at specific wavelengths (either individually or respectively)). Embodiments also provide a software application that can be used to control the multi-modal imaging and/or therapy provided by the device. The software application can be stored (e.g., on memory and/or a (non-transitory) machine-readable (i.e., computer readable) medium, such as a bit file and/or web-based) on the smartphone, tablet, add-on device, or separate standalone device.

In an embodiment, a device for assessing a tissue of a patient by multi-modal imaging can comprise: a plurality of sensors comprising a near-infrared (NIR) camera, a thermal camera, a stereoscopic camera, and/or a visible light camera; at least one first light source; a processor; a memory in operable communication with the processor; a (non-transitory) machine-readable (e.g., computer-readable) medium in operable communication with the processor and the memory; and a software application stored on at least one of the memory and the machine-readable medium. The software application can comprise instructions that, when executed by the processor, perform the following steps: receive data related to the tissue from the plurality of sensors; generate a plurality of maps based on the data related to the tissue received from the plurality of sensors, the plurality of maps comprising a heat map of the tissue, a tissue oxygenation map of the tissue, an area or size map of the tissue, a digital photograph (e.g., a digital color photograph) of the tissue, a melanin map of the tissue, a water map of the tissue, and/or a binary map of tissue size; and provide the plurality of maps to a display in operable communication with the processor. The plurality of maps can be used by a user (e.g., the patient) of the device (e.g., via custom software processing techniques and/or algorithms) to assess the tissue (or any tissue (i.e., can be used for tissue burns, tissue abnormalities, etc.)) of the patient. The device can be a portable, handheld device. The plurality of sensors can further comprise a distance sensor. The least one first light source can comprise a plurality of first light sources (e.g., LEDs) configured for auto-fluorescence imaging. The visible light camera can be or include a red-green-blue (RGB) camera and/or a white light camera. The device can further comprise at least one second light source (e.g., one or more LEDs such as one or more monochromatic LEDs) configured to provide low-level light therapy (LLLT) to the tissue; and the software application can be configured to allow a user to control the at least one second light source to provide LLLT to the tissue (or any tissue). The plurality of maps can comprise a visible light map of the tissue. The heat map of the tissue can be a two-dimensional (2D) heat map or a three-dimensional (3D) heat map; the tissue oxygenation map of the tissue can be a 2D tissue oxygenation map or a 3D tissue oxygenation map; and the visible light map (if present) can be a 2D visible light map or a 3D visible light map (e.g., to determine the tissue depth). The device can also include a stereoscopic camera that can be used for a 3D depth map and/or depth perception of color, oxygenation, and/or heat maps.

The device can comprise a smart device (e.g., a smartphone or a tablet) and an add-on module (which can also be referred to herein as an add-on device) configured to attach to and communicate with the smart device. The NIR camera, the thermal camera, and/or the stereoscopic camera can be disposed on the add-on module, and the display in operable communication with the processor can be disposed on the smart device. The add-on module can comprise at least one of a clip-on attachment and a magnetic attachment configured to attach to the smart device. Each of the add-on module and the smart device can include a processor, a memory, and a (non-transitory) machine-readable (e.g., computer-readable) medium, and each of the processor, the memory, and the machine-readable medium referred to above as part of the device can be disposed in the smart device or in the add-on module (individually or collectively). The device can alternatively be a self-contained standalone device that does not require communication with any smart device to operate, and the self-contained standalone device can comprise the display in operable communication with the processor. Each of the add-on module and the smart device can include a light source driver (e.g., an LED driver or laser diode driver), and the add-on module can also include a lens and/or one or more filters at the source or detector (camera) end. The add-on module can also include an LLLT-related light source; alternatively, LEDs or laser diodes (with appropriate lenses for imaging an entire area instead of a point) can be used for LLLT.

In another embodiment, a method for assessing a tissue of a patient can comprise: scanning the tissue with a device as described herein; and assessing the tissue based on the plurality of maps displayed on a display in operable communication with the processor of the device. The device can have any combination of the features discussed in the previous two paragraphs. The method can further comprise using the software application to control the at least one second light source to provide LLLT to the tissue.

DETAILED DESCRIPTION

Figure 1C:
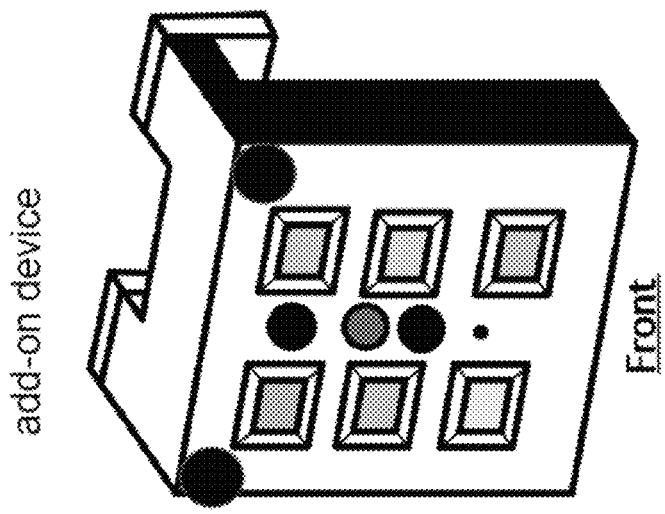
FIG. 1(c) shows an add-on device that can be used with a smartphone or table, according to an embodiment of the subject invention. A device can include the native hardware of the smartphone or tablet (including an internal processor), as well as the external hardware of the add-on device (including the processor thereof). The application can be used to sync the add-on device with a smartphone or table.

Embodiments of the subject invention provide novel and advantageous multi-modal, portable, handheld (e.g., smartphone, tablet, or separate standalone device) imaging technology that can be used for tissue assessment such as wound assessment (e.g., remote wound assessment, such as remote diabetic wound assessment), both visual and physiological, for virtual medicine (VM)-based wound management (e.g., VM-based diabetic foot triage (DFT) and management). Embodiments also provide methods of fabricating the devices and using the devices. The device can be used to take physiological measurements of temperature and/or tissue oxygenation (TO) of a target area (e.g., a wound or wound site) of a patient (e.g., a human patient) to provide assessment (e.g., sub-clinical assessment) to replace, or complement the visual gold-standard clinical assessment (i.e., wound size, color, and epithelization), especially in a remote setting environment. The device can also be used to provide therapy for tissue repair and/or wound healing, apart from the multi-modal imaging of the tissue surface of the patient. For example, light therapy, such as low-level light therapy (LLLT) can be provided (e.g., via one or more light emitting diodes (LEDs), such as one or more LEDs at specific wavelengths (either individually or respectively)). Embodiments also provide a software application that can be used to control the multi-modal imaging and/or therapy provided by the device. The software application can be stored (e.g., on memory and/or a (non-transitory) machine-readable (i.e., computer readable) medium) on the smartphone, tablet, add-on device, or separate standalone device.

Remote temperature sensing (e.g., via a forward looking infrared radar (FLIR) sensor) as a physiologic measure can be used for early warning (or triage) for diabetic foot ulcers (DFUs) in high-risk patients (see also; Lazo-Porras et al., "Implementation of foot thermometry plus mHealth to prevent diabetic foot ulcers: study protocol for a randomized controlled trial," Trials, 17(1): 206, 2016; and Lin et al., "Assessment of lower extremity ischemia using smartphone thermographic imaging," J Vasc Surg Cases Innov Tech, 3(4):205-208, 2017, doi:10.1016/j.jvscit.2016.10.012; both of which are hereby incorporated by reference herein in their entireties). Thermal measurements is associated with perfusion through an area, and a change in temperature (e.g., within 2.2° C.) at the wound interface can be indicative that flow has reduced in that region and the rate of oxyhemoglobin dissociation and oxygen availability may be drastically reduced (see also, Hallock, "Dynamic infrared thermography and smartphone thermal imaging as an adjunct for preoperative, intraoperative, and postoperative perforator free flap monitoring," Plast Aesthet Res, 6:29, 2019, dx.doi.org/10.20517/2347-9264.2019.029; Magnin et al., "Use of infrared thermography to detect early alterations of peripheral perfusion: evaluation in a porcine model," Biomed. Opt. Express, 11, 2431-2446, 2020; and Frykberg et al., "Challenges in the Treatment of Chronic Wounds," Adv Wound Care, 4(9):560-582, 2015, doi:10.1089/wound.2015.0635; all of which are hereby incorporated by reference herein in their entireties). This can result in a decrease in cell proliferation and can therefore slow down the formation of new tissue necessary for wound healing.

Near-infrared (NIR) optical imaging is advantageous in its ability to image subcutaneous tissue oxygenation, which is pertinent to wound healing. In addition to perfusion shown from thermal sensing, oxygen supply to wounds is a vital factor for successful healing as demonstrated from transcutaneous oxygen measurement (TCOM) studies (see also, Ballard et al., "A prospective evaluation of transcutaneous oxygen measurements in the management of diabetic foot problems," Journal of Vascular Surgery, 22(4): 485-492, 1995, which is hereby incorporated by reference herein in its entirety). However, these measurements are obtained from point-based locations and can take up to 20 minutes to capture. Some oxygenation measuring devices can obtain two-dimensional (2D) measurements without contact. Such 2D tissue oxygenation maps can be beneficial in assessing wound progression, and this is not only the case with correlation between visible color maps and oxygenation maps that are coregistered and correlated, but also oxygenation and thermal images (e.g., using NIR and infrared (IR) imaging), which has clinical significance in chronic wound care management. (see also, Lucas et al., "Wound Size Imaging: Ready for Smart Assessment and Monitoring," Advance in Wound Care, 2020, doi: 10.1089/wound.2018.0937; Zhang et al., "Multimodal imaging of cutaneous wound tissue," J Biomed Opt, 20(1):016016, 2015 doi: 10.1117/1.JBO.20.1.016016. PMID: 25604545; PMCID: PMC4300315; Xu et al., "Dual-mode imaging of cutaneous tissue oxygenation and vascular function," Journal of visualized experiments: JoVE, (46): 2095, 2010; and Tewari et al., "Methods for registering and calibrating in vivo terahertz images of cutaneous burn wounds," Biomed Opt Express, 10(1):322-337, 2018, doi:10.1364/BOE.10.000322; all of which are hereby incorporated by reference herein in their entireties). Embodiments of the subject invention provide multi-modal imaging from a visual perspective and a physiological perspective, which can augment standard DFU management, especially for remote virtual assessment of DFUs.

Embodiments of the subject invention provide physiological measurements of temperature and tissue oxygenation provide assessment (e.g., sub-clinical assessment) to replace or complement the visual gold-standard clinical assessment (i.e., wound size, color, and epithelization), especially in a remote setting environment. Detection of temperature fluctuations can be effective for early diagnostics of diabetic feet because ulceration risks are linked to an increase in plantar temperatures. Also, oxygen supply to wounds is a vital factor for successful healing and measurement of oxygen supply to a wound can predict potential to heal sooner than visual assessment alone. Unlike a device that can only obtain 2D wound images or maps, embodiments of the subject invention provide portable, handheld devices capable of measuring (and configured to measure) thermal- and oxygenation-based physiological parameters. Embodiments can also provide digitized visual assessment (e.g., wound size and/or color) using a multi-modal imaging approach, thereby giving multiple clinical assessments of wounds (e.g., diabetic wounds) on a patient.

In addition to physiological assessment of wound healing status, embodiments of the subject invention can also accelerate the wound healing process therapeutically. Generally, wound healing therapies include wound dressings, autografts, allografts, topical agents, stem cell therapy, hyperbaric oxygen treatment, and low-level light therapy (LLLT). LLLT can use LEDs to promote tissue repair in chronic wounds through a thermal photoactive process, exhibiting a biphasic dose response curve. Monochromatic LEDs in particular can be used as therapeutic agents due to their ability to influence cellular sub-structures, in a process known as photobiomodulation (PBM) (see also, De Freitas et al., Proposed Mechanisms of Photobiomodulation or Low-Level Light Therapy, IEEE journal of selected topics in quantum electronics: a publication of the IEEE Lasers and Electro-optics Society, 22(3), 7000417, 2016, doi:10.1109/JSTQE.2016.2561201; which is hereby incorporated by reference herein in its entirety). Photodynamic therapy is a Food and Drug Administration (FDA)-approved treatment in which an extracellular photosensitizing topical agent is applied to a wound bed and, following illumination in the NIR region, forms reactive oxygen species (ROS) (see also, Lubart et al., Photochemistry and photobiology of light absorption by living cells, Photomed Laser Surg, 2006, 24:179-85; which is hereby incorporated by reference herein in its entirety). The ROS are key for cell signaling, regulation of cell cycle, enzyme activation, and nucleic acid/protein synthesis, which are essential for tissue reconstruction.

LLLT is effective in promoting similar wound bed conditions by targeting intracellular photosensitive chromophores that absorb NIR light, leading to an increase in ROS. While the idea that light can stimulate biomolecules sounds intriguing, there is a limit to the magnitude of energy transfer in target elements. Some challenges associated with LLLT are the large variation in reported doses applied when using LEDs and the highly biphasic response observed (see also, Huang et al., Biphasic dose response in low level light therapy, Dose-response: a publication of International Hormesis Society, 7(4), 358-383, 2009, doi:10.2203/dose-response.09-027; which is hereby incorporated by reference herein in its entirety). Ionizing radiation cancer therapies can also exhibit biphasic dose responses largely due to heat dissipation, and theranostics is an attempt to understand the extent of biological response (using biomarkers) for optimized therapy (see also, Choudhury et al., Personalized and Precision Medicine in Cancer: A Theranostic Approach, Curr Radiopharm, 2017, 10(3):166-170, doi: 10.2174/1874471010666170728094008, PMID: 28758574; which is hereby incorporated by reference herein in its entirety). While LLLT is non-ionizing, the process of energy transfer needs to be assessed to prevent or inhibit overworking of cellular components. An LLLT device can use a range of power outputs and wavelengths, and non-contact imaging devices measure changes in oxygenation and blood flow beneath the skin surface. Embodiments of the subject invention can include both LLLT and non-contact imaging (e.g., to measure changes in oxygenation and/or blood flow beneath skin surface), allowing for complete non-contact treatment and objective assessment of therapeutic efficacy for use in complicated chronic wound cases.

In many embodiments, a handheld, portable device can be configured to provide LLLT, for example for the purpose of administering variable dose therapy with the capacity to track physiological changes in tissue oxygenation and temperature in response to applied dose without contact. The LLLT capability can be included in an add-on device for a smartphone or tablet or as a portable hand-held device. Biomarkers for healing predictions can be used to overcome challenges associated with dose delivery in LLLT and identify effective doses for chronic cases.

Figure 1B:
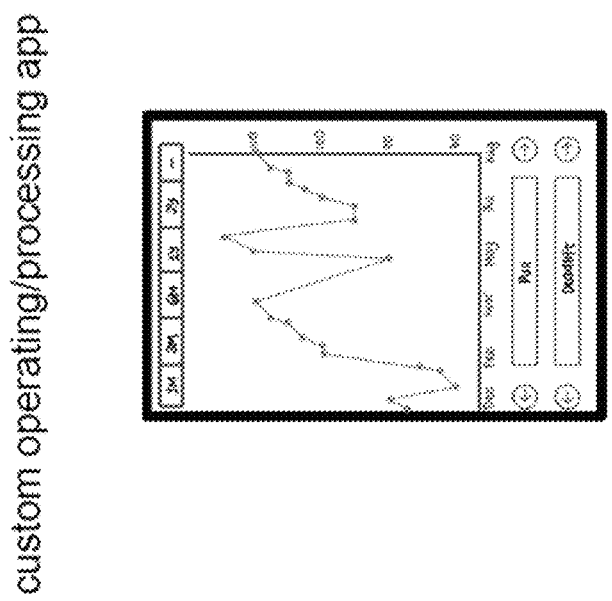
FIG. 1(b) shows another screen of the application from FIG. 1(a).
Figure 1A:
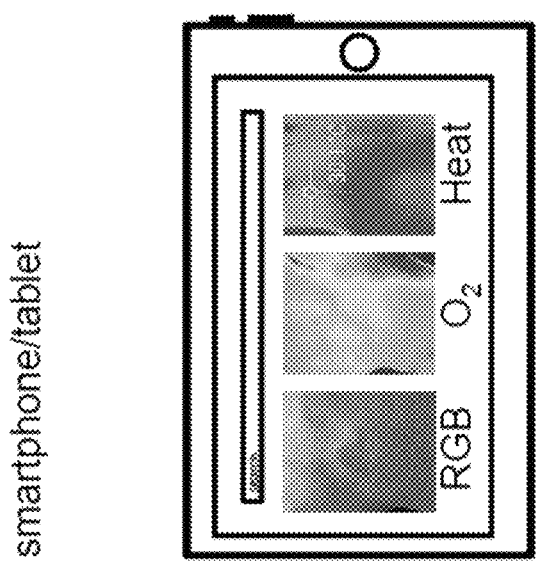
FIG. 1(a) shows a view of a screen of a smartphone, tablet, or standalone handheld device running an application, according to an embodiment of the subject invention.

FIG. 1(a) shows a view of a screen of a smartphone, tablet, or standalone handheld device running an application, according to an embodiment of the subject invention; FIG. 1(b) shows another screen of the application from FIG. 1(a); and FIG. 1(c) shows an add-on device that can be used with a smartphone or table, according to an embodiment. The device can include the native hardware of the smartphone or tablet, if present (including an internal processor), as well as the external hardware of the add-on device, if present (including the processor thereof). If the add-on device is used, the application can be used to sync the add-on device with a smartphone or table. The application can be stored on the smartphone or tablet, if present, the add-on device, or the standalone device (e.g., on memory and/or a (non-transitory) machine-readable (e.g., computer-readable) medium of the respective device).

Figure 2:
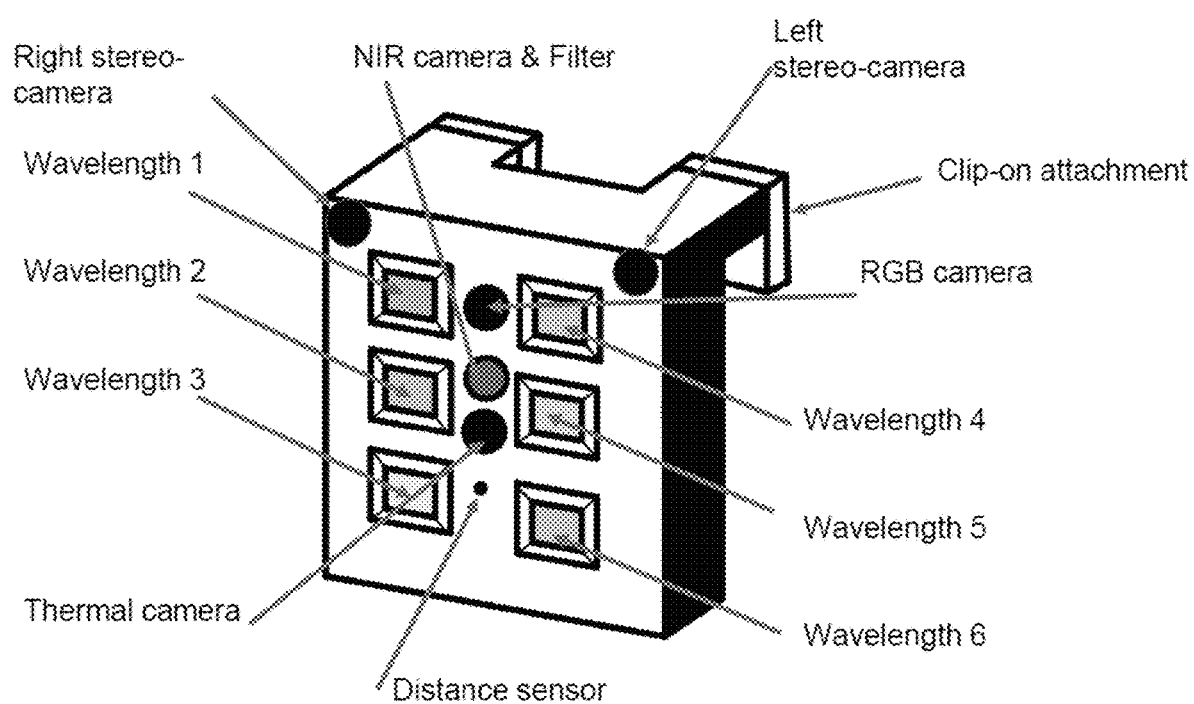
FIG. 2 shows another view of an add-on device that can be used with a smartphone or table, according to an embodiment of the subject invention. Although lights (e.g., light emitting diodes (LEDs) or laser diodes) of six different wavelengths are shown in FIG. 2, this is for exemplary purposes only. More or less lights can be provided on the add-on device. The add-on device can also include a near-infrared (NIR) or infrared (IR) camera and/or filter, a red/green/blue (RGB) camera, a distance sensor, a thermal camera, a stereoscopic camera, an additional light source for low-level light therapy (LLLT), and/or a means of attaching to a smartphone or tablet (e.g., a clip-on attachment and/or a magnetic attachment).

FIG. 2 shows another view of an add-on device that can be used with a smartphone or table, according to an embodiment of the subject invention. The add-on device can include an NIR and/or IR camera and/or filter, a red/green/blue (RGB) camera, a white light camera, a distance sensor, a thermal camera, and/or a means of attaching to a smartphone or tablet (e.g., a clip-on attachment and/or a magnetic attachment). The device can also include lights, such as LEDs (or laser diodes or any other appropriate light source that is in the wavelength range of interest), and each light can be monochromatic (i.e., providing light of one specific wavelength) or can be capable of providing different color lights. Although lights (e.g., LEDs, laser diodes, etc.) of six different wavelengths are shown in FIG. 2, this is for exemplary purposes only; more or less light sources or lights can be provided on the add-on device. The lights can be used for providing imaging (e.g., auto-fluorescence imaging) and/or LLLT. In embodiments where the device is a standalone device, the standalone device can include some or all of the elements shown in FIG. 2—an NIR and/or IR camera and/or filter, an RGB camera, a white light camera, a distance sensor, a thermal camera, and/or at least one light (e.g., LED, laser diode, etc.). The standalone device can also include a processor, memory, a (non-transitory) machine-readable (e.g., computer-readable) medium, and/or a display. The add-on module can have one set of light sources for imaging/diagnostic purposes and/or a second set of light sources for therapeutics/therapy. These light sources may be in sets of any number (e.g., four, three, two, five, six, etc.) based on the chosen wavelengths of interest. In some cases, the same light sources (of similar wavelengths) can be used at different power settings to be used for imaging or therapy. In a different case, a completely different set of light sources (even if some wavelengths overlaps) may be used to toggle between imaging and therapy application. One or more stereoscopic cameras (or "stereo-cameras") can be included on the add-on device.

Figures 3A, 3B:
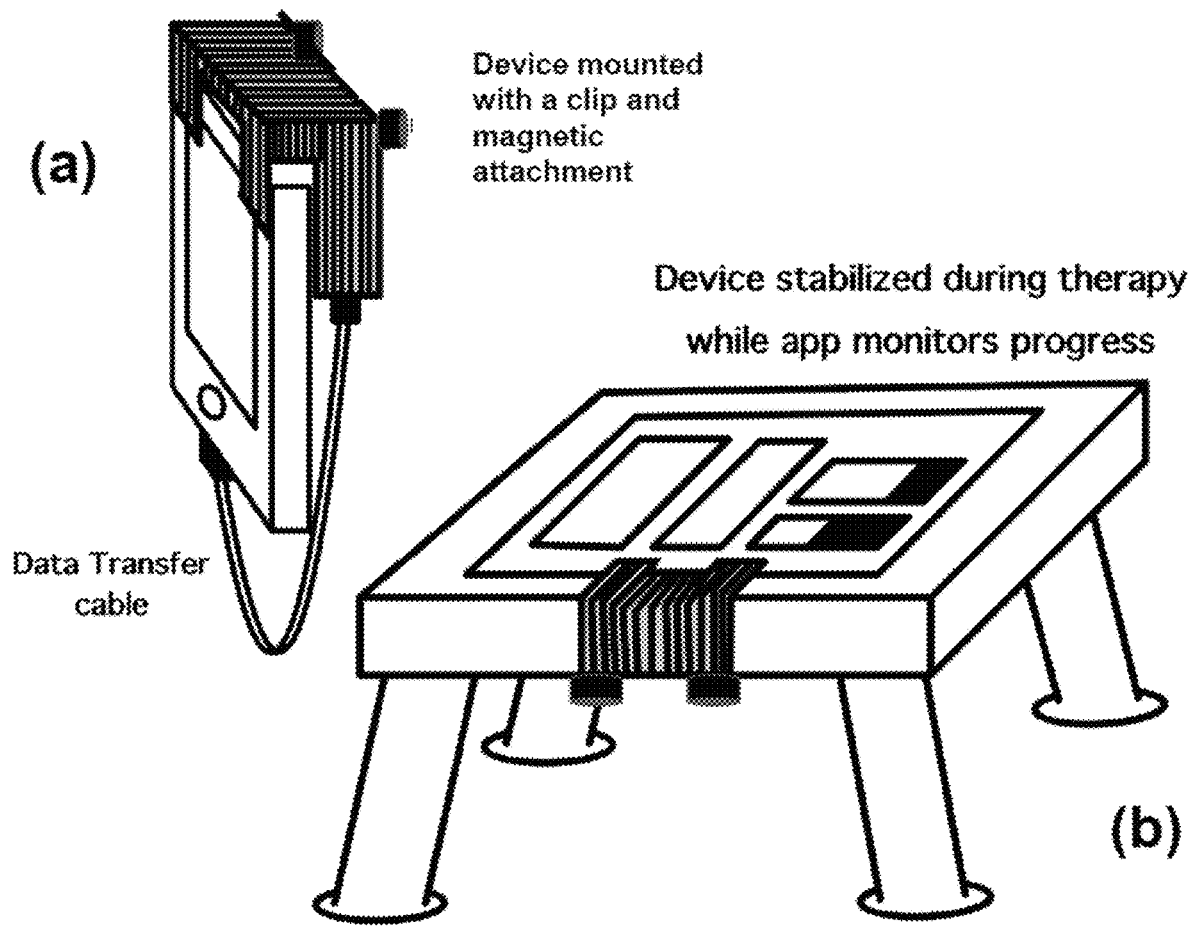
FIG. 3(a) shows a schematic view of an add-on device attached to a tablet, according to an embodiment of the subject invention. The add-on device could be similarly mounted to a smartphone. The add-on device can be mounted to a tablet or smartphone using, for example, a mechanical clip and/or a magnetic clip. Data transfer between external device and internal tablet/smartphone processor can be achieved wirelessly (e.g., via Bluetooth, Wi-Fi, or other wireless means) and/or in a wired manner (e.g., via a cable as depicted in FIG. 3(a)).
FIG. 3(b) shows a schematic view of an add-on device mounted to a tablet during therapy and/or imaging, according to an embodiment of the subject invention. The device can be stabilized (e.g., by placing on a structure and/or by using legs included as part of the add-on device) in order to ensure therapy is delivered uniformly (or mostly uniformly) and with ease for the user, who only needs to situate the device directly over the region designated for applied therapy. The application can be used for controlling the add-on device and/or the smartphone or tablet in terms of delivering therapy and/or in terms of diagnostic syncing of NIR light with the NIR sensor. The application can also monitor the extent of applied therapy.

FIG. 3(a) shows a schematic view of an add-on device attached to a tablet, according to an embodiment of the subject invention. The add-on device could be similarly mounted to a smartphone. The add-on device can be mounted to a tablet or smartphone using, for example, a mechanical clip and/or a magnetic clip. Data transfer between the add-on device and internal tablet/smartphone processor can be achieved wirelessly (e.g., via Bluetooth, Wi-Fi, or other wireless means) and/or in a wired manner (e.g., via a cable as depicted in FIG. 3(a)).

FIG. 3(b) shows a schematic view of an add-on device mounted to a tablet during therapy (e.g., LLLT therapy), according to an embodiment of the subject invention. The device can be stabilized (e.g., by placing on a structure and/or by using legs included as part of the add-on device) in order to ensure therapy is delivered uniformly (or mostly uniformly) and with ease for the user, who only needs to situate the device directly over the region designated for applied therapy. The application can be used for controlling the add-on device and/or the smartphone or tablet in terms of delivering therapy and/or in terms of diagnostic syncing of NIR light with the NIR sensor. The application can also monitor the extent of applied therapy. In embodiments where the device is a standalone device, the standalone device can provide therapy (e.g., LLLT therapy) in much the same manner shown in FIG. 3(b).

Figure 4:
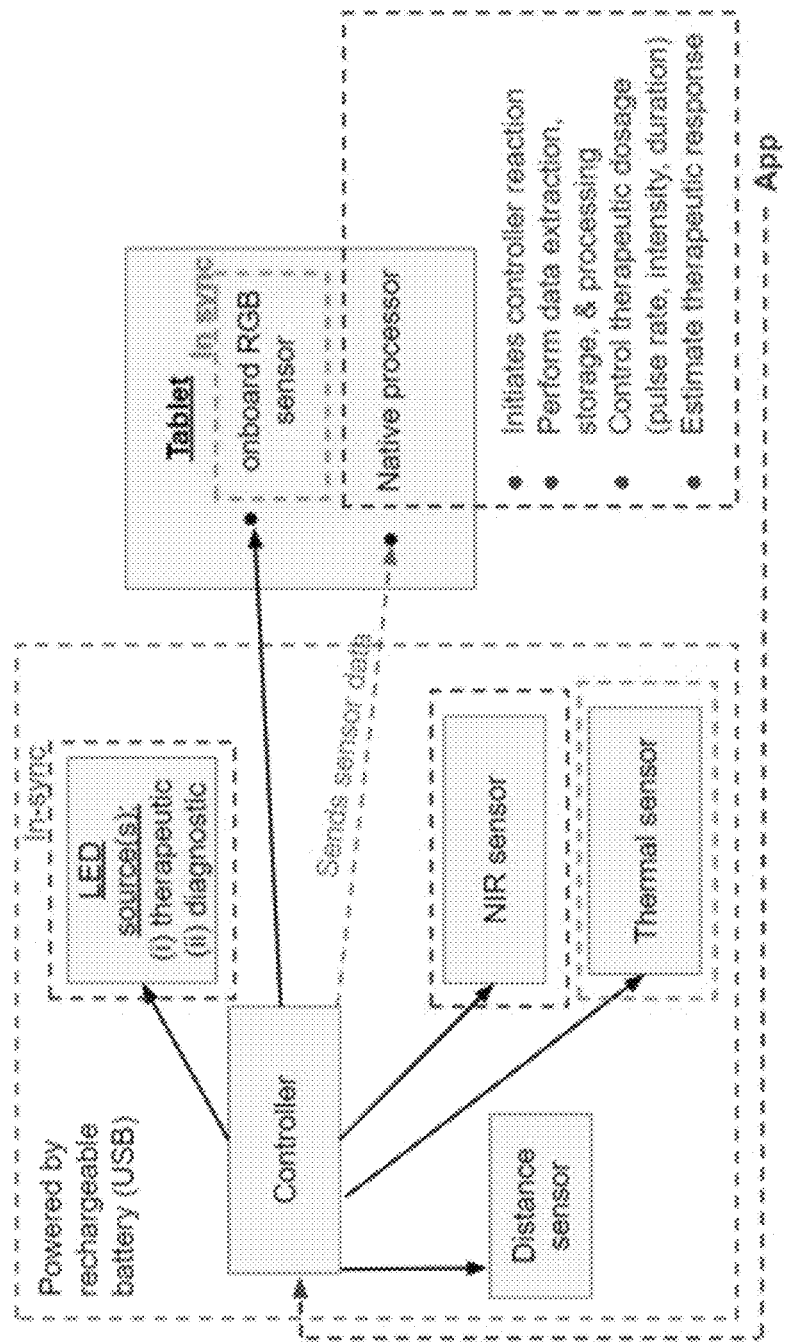
FIG. 4 shows a schematic view of parts of a device according to an embodiment of the subject invention. The external device (e.g., add-on device and/or smartphone or tablet, or a standalone device) can control multiple sensors and sources simultaneously, and such sensors and sources can be synced by the application on the smartphone or tablet (or standalone device). The syncing/control can include that of the native smartphone/tablet (if present) camera.

FIG. 4 shows a schematic view of parts of a device according to an embodiment of the subject invention. The external device (e.g., add-on device and/or smartphone or tablet, or a standalone device) can control multiple sensors and sources simultaneously, and such sensors and sources can be synced by the application on the smartphone or tablet (or standalone device). The syncing/control can include that of the native smartphone/tablet (if present) camera.

Figure 5:
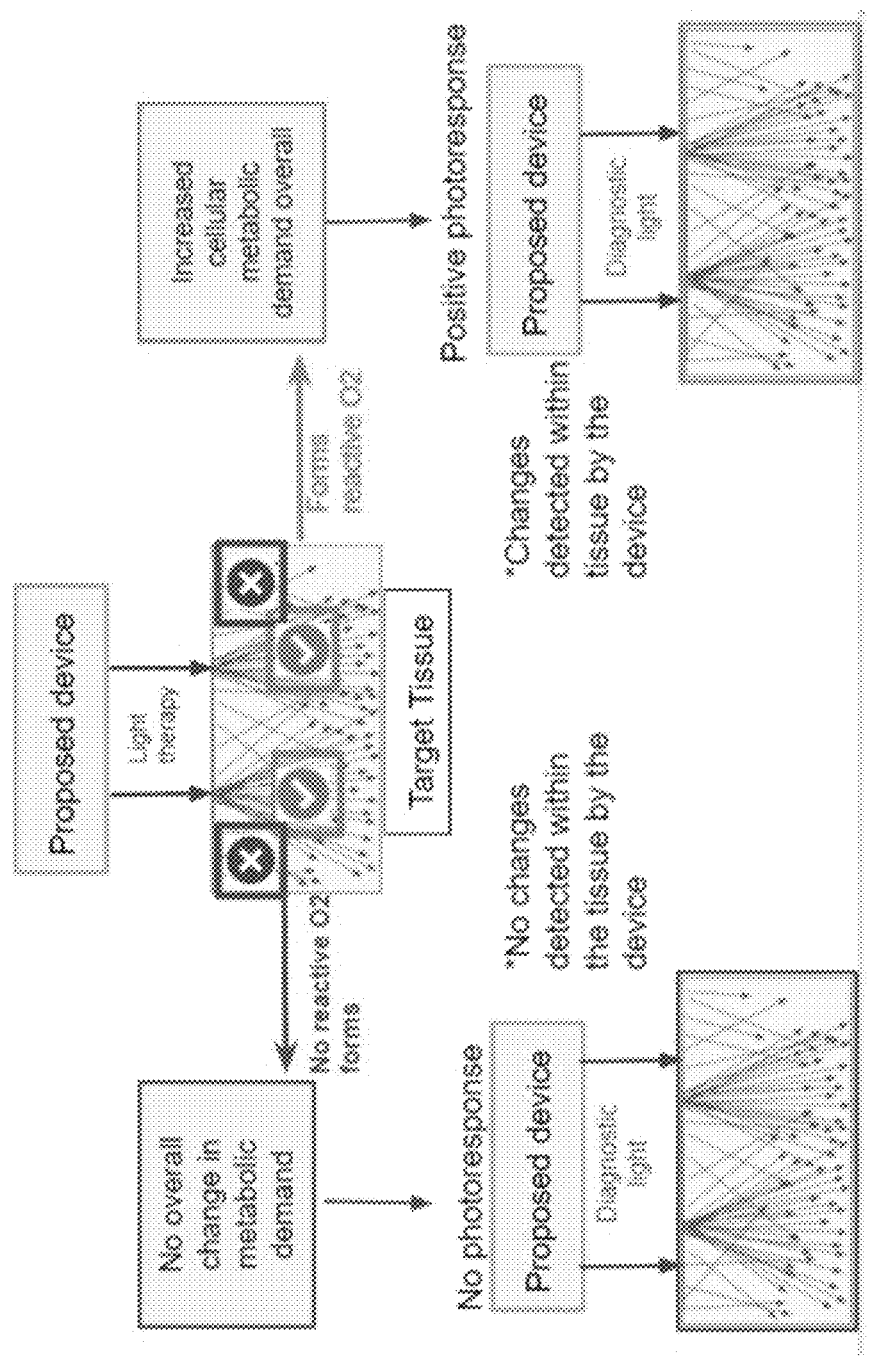
FIG. 5 shows a schematic view demonstrating a theranostic approach in algorithm development for a custom software application, according to an embodiment of the subject invention. When therapeutic light is applied to tissue, energy is either sufficient for absorption by target chromophores (e.g., forms reactive $O_2$ species) or no energy is delivered to the tissue (no reactive $O_2$ species formed). A positive photoresponse can induce tissue activity (i.e., in wounds this means healing) and increase the overall cellular metabolic demand. In turn, oxygenation changes can be determined using, for example, two-dimensional (2D) tissue oxygenation maps (e.g., using the imaging aspect of the add-on device).

FIG. 5 shows a schematic view demonstrating a theranostic approach in algorithm development for a custom software application, according to an embodiment of the subject invention. The custom software application can be the application (or software application) referred to elsewhere herein. When therapeutic light is applied to tissue, energy is either sufficient for absorption by target chromophores (e.g., forms ROS) or no energy is delivered to the tissue (no ROS formed). A positive photoresponse can induce tissue activity (i.e., in wounds this means healing) and increase the overall cellular metabolic demand. In turn, oxygenation changes can be determined using, for example, 2D tissue oxygenation maps.

Figure 6:
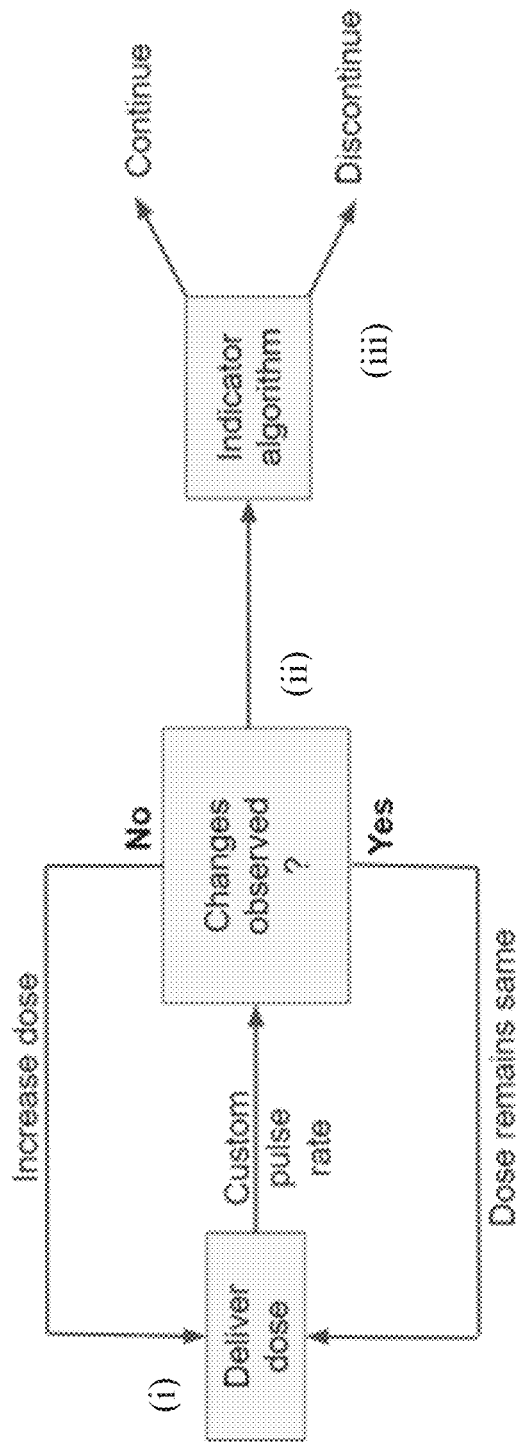
FIG. 6 shows a chart of approaches of embodiments of the subject invention. Represented are: (i) dose delivery related to pulse rate (i.e., the frequency of the laser pulse or laser diode pulse) and intensity; (ii) diagnostic assessment of changes in terms of tissue oxygenation and thermal maps; and (iii) theranostic indicator algorithm to predict if therapy is completed or further recommended.

FIG. 6 shows a chart of objects that can be accomplished by embodiments of the subject invention. Represented are: (i) dose delivery related to pulse rate (frequency of the laser pulse (or laser diode pulse) and intensity; (ii) diagnostic assessment of changes in terms of tissue oxygenation and thermal maps; and (iii) theranostic indicator algorithm to predict if therapy is completed or further recommended.

In an embodiment, a smartphone-based or tablet-based add-on device (or a standalone device) can perform diagnostics via physiological assessment of thermal changes and/or tissue oxygenation changes of tissue. An LLLT module can optionally be included, such that the device would also be a theranostics device. The device can perform multi-modal imaging (e.g., NIR imaging, IR imaging, thermal imaging, white light imaging, RGB imaging, and/or auto fluorescence imaging) and/or LLLT. The device can include light sources in specific or broad-spectrum visible light and NIR wavelengths, thermal or IR sensors (or detectors), an NIR sensor (or detector), a distance sensor, drivers for light sources and/or sensors, optical filters, polarizers, diffusers, reflectors, and/or a wireless (e.g., Bluetooth and/or Wi-Fi) platform.

If an add-on device or module is used, the smartphone's (or tablet's) own camera(s) can be used along with the add-on device/module (as can an NIR related filter), and these can be synced for multi-modal imaging via a software application for data acquisition. Alternatively, a separate NIR-sensitive camera can be included in the add-on device/module, and the smartphone/tablet can be used for data acquisition and/or analysis via a software application. In some embodiments, a completely independent handheld standalone device can have all modules/functionalities (e.g., thermal imaging, NIR imaging to obtain tissue oxygenation measurements, and/or LLLT module), one or more of which can be integrated into the device.

A custom software application can be provided/utilized for data acquisition from one or more of the imaging approaches (NIR imaging, thermal imaging, RGB imaging, white light imaging, and/or auto fluorescence imaging at specific wavelength(s) of choice); the images obtained from different imaging approaches can also be coregistered. The application can be synced with the add-on device/module and the smartphone's/tablet's camera (e.g., via Bluetooth, Wi-Fi, a cable, or similar technology). The application can be used for data pre-processing and/or analysis from one or more of the images (e.g., single- or multi-wavelength NIR images, thermal images, RGB images, white light images, and/or auto-fluorescence images at specific wavelength(s) of choice) that are displayed individually or co-registered onto each other. The application can be used for processing multi-wavelength images to generate tissue oxygenation maps (e.g., in terms of oxy-hemoglobin, deoxy-hemoglobin, total hemoglobin, and/or oxygen saturation) along with thermal maps, auto-fluorescence maps, RGB maps, and/or white light maps. The application can be used to perform co-registration and/or image segmentation of each or any of these images with respect to each other, or all images into a single co-registered and/or segmented image. Segmentation can be manual or can be done using artificial intelligence (e.g., deep learning, machine learning, and/or convolutional neural networks). The device (e.g., add-on device/module and/or standalone device can include one or more LLLT-based LEDs or laser diodes (which can be at specific wavelengths) to allow therapeutic application in tissue repair and/or wound healing, apart from multi-modal imaging of the tissue surface. The software application can be used to control the LLLT (e.g., the one or more LLLT-based LEDs) for therapeutic applications, and the controls can include controlling dosage, power, intensity, and/or time.

United States Patent Application Publication No. 2019/0008387 and United States Patent Application Publication No. 2020/0352515 both described devices that may have some features in common with certain aspects of embodiments of the subject invention, and both are hereby incorporated by reference herein in their entireties. United States Patent Application Publication No. 2020/0352515 describes a smartphone-based device that can physiologically measure for tissue oxygenation changes in wounds apart from providing 2D visual wound images (see also, Kaile et al., "Development and validation of a smartphone based near-infrared optical imaging device to measure physiological changes in-vivo," Micromachines 10(3): 180, 2019, doi: 10.3390/mi10030180; Kaile et al., "Low-cost smartphone-based imaging device to detect subsurface tissue oxygenation of wounds," SPIE Proceedings, Vol. 10869, Optics and Biophotonics in Low-Resource Settings V, San Francisco, US, doi: 10.1117/12.2510425, 2019; and Kaile et al., Development of a Smartphone-Based Optical Device to Measure Hemoglobin Concentration Changes for Remote Monitoring of Wounds, Biosensors, 2021, 11(6):165, doi.org/10.3390/bios11060165; all of which are hereby incorporated by reference herein in their entireties). The mechanism for tissue oxygenation sensing described in United States Patent Application Publication No. 2020/0352515 can be utilized for tissue oxygenation sensing in devices of embodiments of the subject invention.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A device for assessing a tissue of a patient by multi-modal imaging, the device comprising:
    a plurality of sensors comprising a near-infrared (NIR) camera, a thermal camera, and a visible light camera;
    a plurality of first light sources;
    a processor;
    a memory in operable communication with the processor;
    a machine-readable medium in operable communication with the processor and the memory; and
    a software application stored on at least one of the memory and the machine-readable medium, the software application comprising instructions that, when executed by the processor, perform the following steps:
        receiving data related to the tissue from the plurality of sensors;
        generating a plurality of maps based on the data related to the tissue received from the plurality of sensors, the plurality of maps comprising a heat map of the tissue and a tissue oxygenation map of the tissue; and
        providing the plurality of maps to a display in operable communication with the processor;
    the device being a portable, handheld device;
    the plurality of first light sources comprising at least four first light sources configured to provide low-level light therapy (LLLT) to the tissue, each of the first light sources providing light at a different wavelength from each of the other first light sources;
    the software application being configured to allow a user to control the plurality of first light sources to provide LLLT to the tissue;
    the device further comprising:
        a smart device that is a smartphone or a tablet; and
        an add-on module configured to attach to and communicate with the smart device;
    the NIR camera, the plurality of first light sources, and the thermal camera being disposed on the add-on module; and
    the display in operable communication with the processor being disposed on the smart device.

2. The device according to claim 1, the plurality of sensors further comprising a distance sensor.

3. The device according to claim 1, the plurality of first light sources being further configured for auto-fluorescence imaging.

4. The device according to claim 1, the add-on module comprising at least one of a clip-on attachment and a magnetic attachment configured to attach to the smart device.

5. The device according to claim 1, the processor, the memory, and the machine-readable medium being disposed in the smart device.

6. The device according to claim 1, the plurality of sensors further comprising a stereoscopic camera disposed on the add-on module.

7. The device according to claim 1, the plurality of sensors further comprising a stereoscopic camera.

8. The device according to claim 1, further comprising at least one second light source configured for auto-fluorescence imaging.

9. The device according to claim 1, each first light source being a light emitting diode (LED) or a laser diode.

10. The device according to claim 1, the plurality of maps comprising a visible light map of the tissue, a melanin map of the tissue, and a water map of the tissue.

11. The device according to claim 1, the heat map of the tissue being a two-dimensional (2D) heat map, and the tissue oxygenation map of the tissue being a 2D tissue oxygenation map.

12. A method for assessing a tissue of a patient, the method comprising:
    scanning the tissue with a device that is portable and handheld, the device comprising:
        a plurality of sensors comprising a near-infrared (NIR) camera, a thermal camera, and a visible light camera;
        a plurality of first light sources, the plurality of first light sources comprising at least four first light sources configured to provide low-level light therapy (LLLT) to the tissue, each of the first light sources providing light at a different wavelength from each of the other first light sources;
        a smart device that is a smartphone or a tablet;
        an add-on module configured to attach to and communicate with the smart device;
        a processor;
        a memory in operable communication with the processor;
        a machine-readable medium in operable communication with the processor and the memory; and
        a software application stored on at least one of the memory and the machine-readable medium, the software application being configured to generate a plurality of maps based on data related to the tissue received from the plurality of sensors, the plurality of maps comprising a heat map of the tissue and a tissue oxygenation map of the tissue, the software application being configured to allow a user to control the plurality of first light sources to provide LLLT to the tissue;
    assessing the tissue based on the plurality of maps displayed on a display in operable communication with the processor; and
    using the software application to control the plurality of first light sources to provide LLLT to the tissue;
    the plurality of sensors further comprising a stereoscopic camera;
    the NIR camera, the thermal camera, the plurality of first light sources, and the stereoscopic camera being disposes on the add-on module;
    the display in operable communication with the processor being disposed on the smart device.

13. The method according to claim 12, the plurality of sensors further comprising a distance sensor;
    the plurality of first light sources being further configured for auto-fluorescence imaging;
    the plurality of sensors further comprising a stereoscopic camera;

the plurality of maps comprising a visible light map of the tissue, a melanin map of the tissue; and a water map of the tissue, the heat map of the tissue being a two-dimensional (2D) heat map; and the tissue oxygenation map of the tissue being a 2D tissue oxygenation map.

14. The method according to claim 12, the plurality of sensors further comprising a stereoscopic camera; and the stereoscopic camera being disposed on the add-on module.

15. The method according to claim 12, the device further comprising at least one second light source configured for auto-fluorescence imaging.

16. The method according to claim 12, each first light source being a light emitting diode (LED) or a laser diode.

17. A device for assessing a tissue of a patient by multi-modal imaging, the device comprising:

a plurality of sensors comprising a near-infrared (NIR) camera, a thermal camera, a visible light camera, a stereoscopic camera, and a distance sensor;

a plurality of first light sources, the plurality of first light sources comprising at least four first light sources configured to provide low-level light therapy (LLLT) to the tissue, each of the first light sources providing light at a different wavelength from each of the other first light sources;

at least one second light source for auto-fluorescence imaging;

a processor;

a memory in operable communication with the processor;

a machine-readable medium in operable communication with the processor and the memory; and a software application stored on at least one of the memory and the machine-readable medium, the software application comprising instructions that, when executed by the processor, perform the following steps:

receiving data related to the tissue from the plurality of sensors;

generating a plurality of maps based on the data related to the tissue received from the plurality of sensors, the plurality of maps comprising a heat map of the tissue, a tissue oxygenation map of the tissue, a visible light map of the tissue, a melanin map of the tissue, and a water map of the tissue; and providing the plurality of maps to a display in operable communication with the processor;

the device being a portable, handheld device;

the software application being configured to allow a user to control the plurality of first light sources to provide LLLT to the tissue;

each first light source being a light emitting diode (LED) or a laser diode;

the device comprising:

a smart device that is a smartphone or a tablet; and an add-on module configured to attach to and communicate with the smart device;

the NIR camera, the thermal camera, the plurality of first light sources, and the distance sensor being disposed on the add-on module;

the display in operable communication with the processor being disposed on the smart device; and the add-on module comprising at least one of a clip-on attachment and a magnetic attachment configured to attach to the smart device.

\* \* \* \* \*